United States Patent [19]

Gerry

[11] Patent Number: 5,327,908
[45] Date of Patent: Jul. 12, 1994

[54] SURGICAL APPARATUS FOR MEASURING BODY TISSUE

[75] Inventor: Stephen W. Gerry, Bethel, Conn.

[73] Assignee: United States Surgical Corporation, Norwalk, Conn.

[21] Appl. No.: 2,061

[22] Filed: Jan. 8, 1993

[51] Int. Cl.⁵ .............................. A61B 5/103
[52] U.S. Cl. ............................................ 128/774
[58] Field of Search ............ 128/751, 754, 774; 606/170, 167, 205

[56] References Cited

U.S. PATENT DOCUMENTS

| | | |
|---|---|---|
| 2,002,594 | 5/1935 | Wappler et al. |
| 2,034,785 | 3/1936 | Wappler. |
| 2,790,437 | 4/1957 | Moore. |
| 3,506,012 | 4/1970 | Brown. |
| 3,871,379 | 3/1975 | Clarke. |
| 3,895,636 | 7/1975 | Schmidt. |
| 3,964,468 | 6/1976 | Schulz. |
| 4,038,987 | 8/1977 | Komiya. |
| 4,064,881 | 12/1977 | Meredith. |
| 4,106,508 | 8/1978 | Berlin. |
| 4,122,856 | 10/1978 | Mosior et al. |
| 4,128,099 | 12/1978 | Bauer. |
| 4,169,476 | 10/1979 | Hiltebrandt. |
| 4,233,743 | 11/1980 | Flick ............................... 33/143 C |
| 4,312,363 | 1/1982 | Rothfuss et al. ................. 128/774 |
| 4,512,343 | 4/1985 | Falk et al. ........................ 174/111 |
| 4,522,206 | 6/1985 | Whipple et al. ................. 128/752 |
| 4,569,131 | 2/1986 | Falk et al. ........................ 128/751 |
| 4,590,936 | 5/1986 | Straub et al. .................... 128/305 |
| 4,646,751 | 3/1987 | Maslanka ......................... 128/751 |
| 4,662,371 | 5/1987 | Whipple et al. ................. 604/22 |
| 4,674,501 | 6/1987 | Greenberg ....................... 128/305 |
| 4,712,545 | 12/1987 | Honkanen ........................ 128/751 |
| 4,760,848 | 8/1988 | Hasson ............................. 294/115 |
| 4,785,825 | 11/1988 | Romaniuk et al. .............. 128/751 |
| 4,898,157 | 2/1990 | Messroghli et al. ............. 606/147 |
| 4,944,093 | 7/1990 | Falk .................................. 606/174 |
| 4,976,723 | 12/1990 | Schad ............................... 606/170 |
| 4,986,825 | 1/1991 | Bays et al. ....................... 604/22 |
| 4,994,024 | 2/1991 | Falk .................................. 604/22 |
| 4,994,079 | 2/1991 | Genese et al. ................... 606/206 |
| 5,040,715 | 8/1991 | Green et al. ..................... 227/176 |
| 5,071,430 | 12/1991 | de Salis et al. .................. 606/219 |
| 5,147,373 | 9/1992 | Ferzli ................................ 606/144 |
| 5,152,780 | 10/1992 | Honkanen et al. .............. 606/205 |

FOREIGN PATENT DOCUMENTS

| | | |
|---|---|---|
| 0380874A1 | 8/1990 | European Pat. Off. . |
| 8900376.4 | 4/1989 | Fed. Rep. of Germany. |
| 3802651 | 8/1989 | Fed. Rep. of Germany. |
| 8903782.0 | 10/1989 | Fed. Rep. of Germany. |

Primary Examiner—Max Hindenburg

[57] ABSTRACT

An apparatus is provided for approximating the jaw structure of surgical instrumentation. The apparatus includes a first jaw structure and a second jaw structure. The second jaw structure is disposed in spaced relation to and connected with the first jaw structure. The first and second jaw structure are interconnected for measurement of body tissue. An elongated endoscopic section extends proximally from the first and second jaw structure. A remote actuation member is connected to the proximal end of the elongated endoscopic section and is provided for relative movement of the first and second jaw structure. The apparatus further includes at least one indicating device which exhibits movement of the jaw structure.

26 Claims, 6 Drawing Sheets

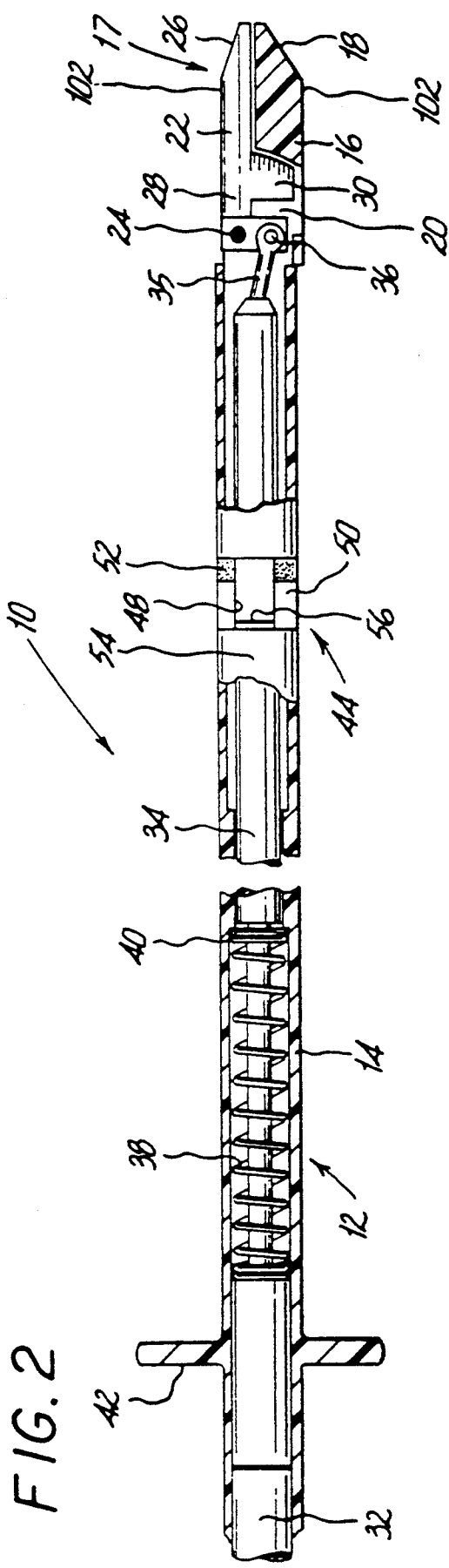
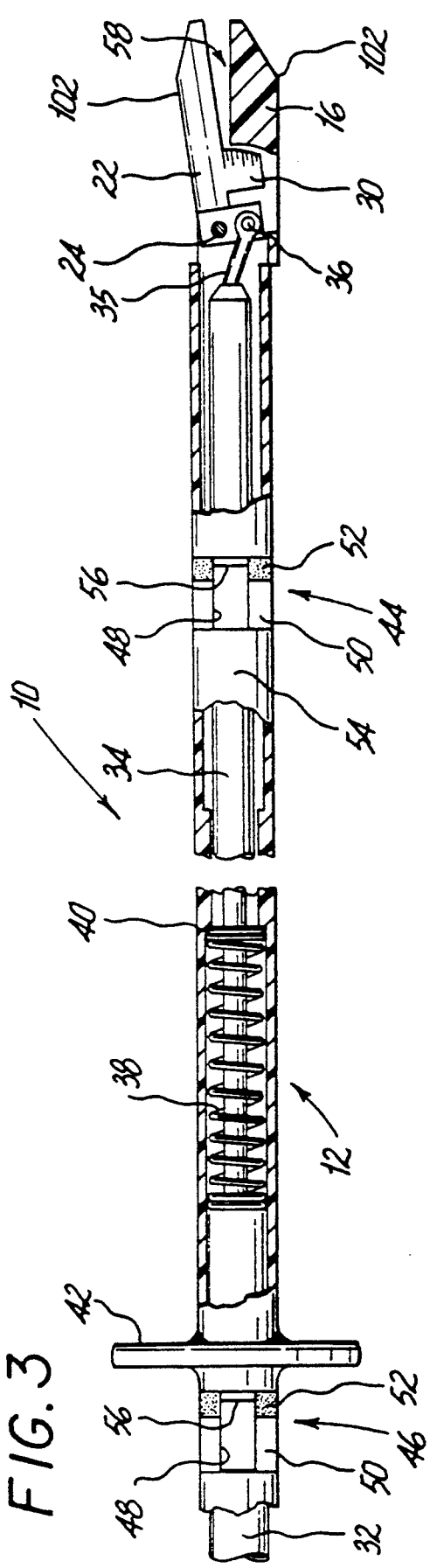
FIG. 2
FIG. 3

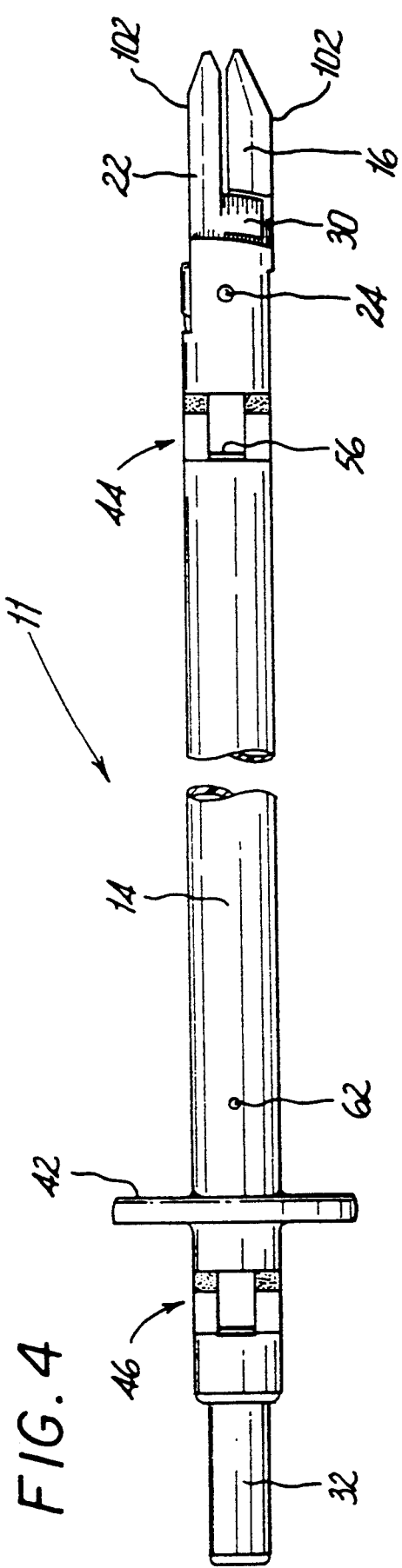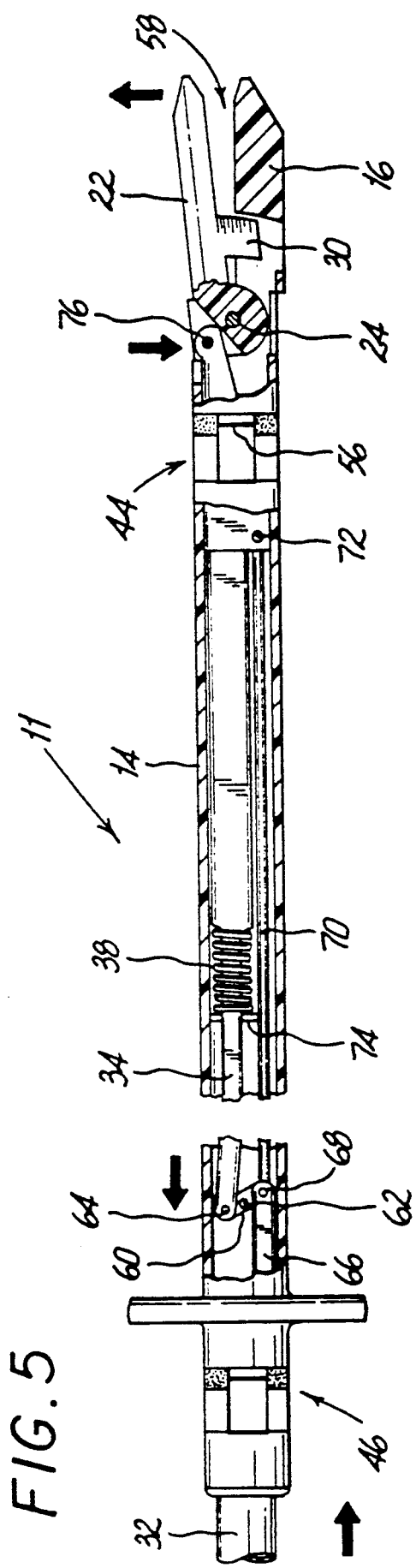
FIG. 4
FIG. 5

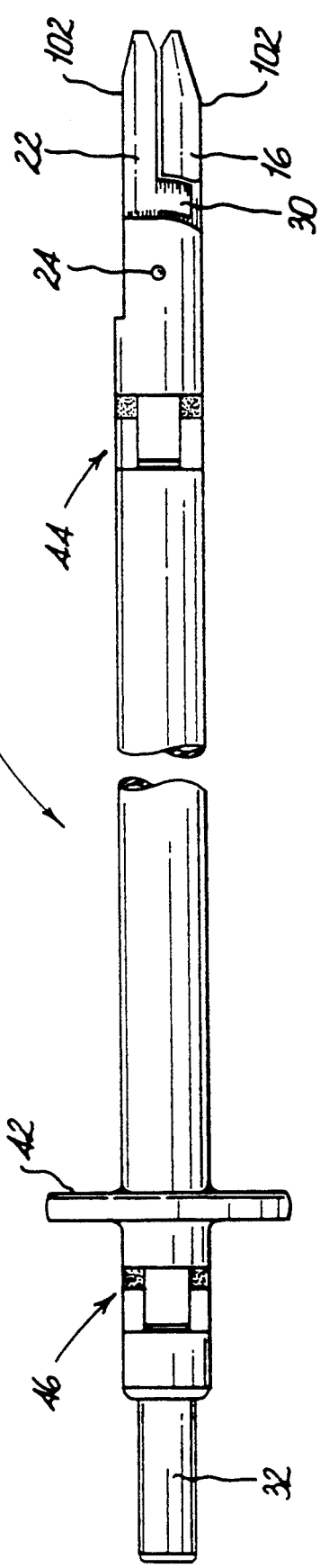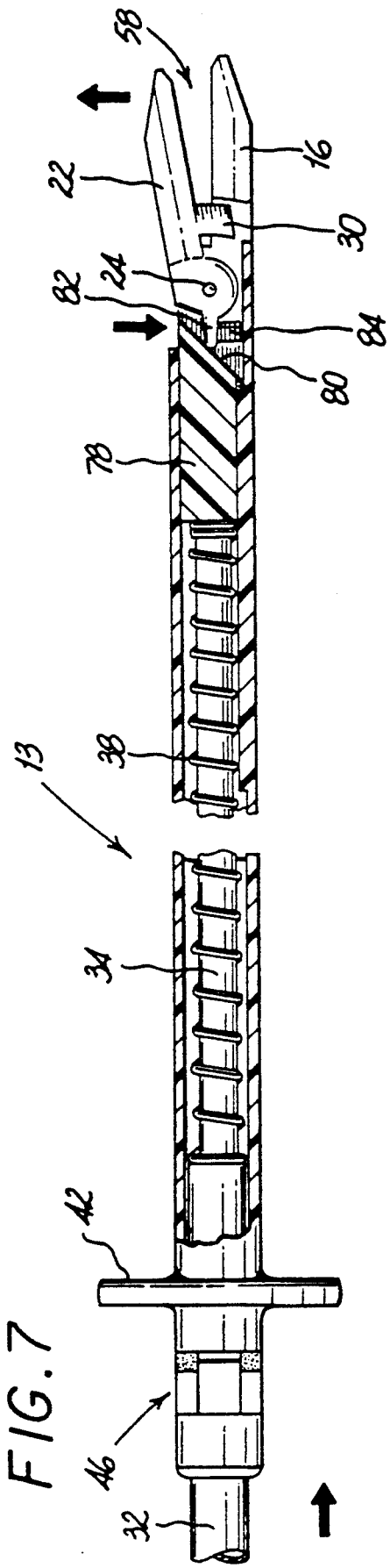

SURGICAL APPARATUS FOR MEASURING BODY TISSUE

BACKGROUND OF THE INVENTION

1. Field of the Invention

The present invention relates generally to approximating apparatus for surgical instrumentation and more particularly to surgical apparatus for measuring body tissue which includes scissor-like approximation of jaw structure.

2. Description of the Related Art

Measuring body tissue during surgical procedures requires precise tissue thickness readings with definitive results under demanding time restraints. In these procedures accuracy and precision are important. Further, measurement indication should be visually accessible to ensure speed and accuracy of tissue measurement. The ease and efficiency of the tissue capturing step is also extremely important if the surgical procedure is to be carried out in an predetermined manner meeting surgical requirements.

Generally, tissue measuring devices for surgical procedures include a jaw structure. Manipulation of the jaw structure is necessary to capture the desired tissue. A typical surgical tissue measuring device is disclosed in U.S. Pat. No. 4,312,363 (Rothfuss et al.). The Rothfuss et al. device may be inserted into the body cavity through a surgical opening. The design and size of the tissue measuring device necessitates a surgical opening that is substantially large, or a body cavity made accessible during extensive surgical procedures. The device further includes jaw structure for capturing tissue. The jaw structure is actuated by a handle portion which may include a scaled portion for indicating tissue thickness.

One disadvantage to typical tissue measuring devices is they require a substantially large surgical opening to access the desired tissue and are therefore incapable and/or undesirable for use in endoscopic or laparoscopic procedures where accessibility is extremely limited. Moreover, due to limited accessibility, manipulation of the jaw structure may be problematic.

Accordingly, there is a defined need for a tissue measuring device that is applicable for endoscopic and/or laparoscopic procedures. It would also be desirable to provide a tissue measuring device which provides ease of operation during endoscopic and/or laparoscopic procedures. It would also be desirable to provide pivotal jaw structure which provides substantially problem free operation of the device. It would further be desirable to provide a tissue measuring device which is capable of controlled approximation of jaw structure. It is also desirable to provide a tissue measuring device that surely and accurately measures body tissue endoscopic and/or laparoscopically. It would further be desirable to provide positive and visually accessible indication of such tissue measurement during endoscopic and/or laparoscopic use of the device.

SUMMARY OF THE INVENTION

An apparatus is provided for approximating the jaw structure of surgical instrumentation to measure dimensions of selected tissue endoscopically and/or laparoscopically. The apparatus includes a first jaw structure having a distal working end and a second jaw structure disposed in spaced relation to and pivotally connected with the first jaw structure. The second jaw structure has a distal working end for interaction with the first jaw structure's distal working end. The first and second jaw structures are configured and dimensioned for engaging tissue.

Approximating structure is provided for approximating the first and second jaw structures. The approximating structure includes an elongated endoscopic section. The elongated endoscopic section is coupled at its distal end to the first and second jaw structures. A remote actuation member is positioned adjacent the proximal end of the endoscopic section for remotely actuating the first jaw structure in relation to the second jaw structure. This permits working interaction between the distal working ends of the first and second jaw structures. The pivotal action of the jaw structure provides simplicity and ease of operation by the approximating structure. The apparatus further includes indicating means which indicates movement of the movable jaw structure in a measured fashion. The indicating means are readily visible during endoscopic and/or laparoscopic procedures.

The tissue measuring device provided may also include various approximating structure for moving the first and second jaw structures in a reliable and measured fashion.

BRIEF DESCRIPTION OF THE DRAWINGS

The foregoing features of the present invention will become more readily apparent and will be understood by referring to the following detailed description of preferred embodiments of the invention, which are described hereinbelow with reference to the drawings wherein:

FIG. 2 is a side view in partial cross-section taken along line 2—2 of FIG. 1 illustrating the tissue measuring apparatus in a closed position.

FIG. 3 is a side view in partial cross-section illustrating the tissue measuring apparatus of FIG. 2 with jaw structures in an open position;

FIG. 4 is a side-elevational view illustrating a tissue measuring apparatus according to a second embodiment of the present invention;

FIG. 5 is a side view in partial cross-section of the apparatus of FIG. 4 illustrating the tissue measuring apparatus having the jaw structures in an open position;

FIG. 6 is a side-elevational view illustrating a tissue measuring apparatus according to a third embodiment of the present invention;

FIG. 7 is a side view in partial cross-section of the apparatus of FIG. 6 illustrating the jaw structures in an open position;

DETAILED DESCRIPTION OF THE PREFERRED EMBODIMENTS

Figure 1:
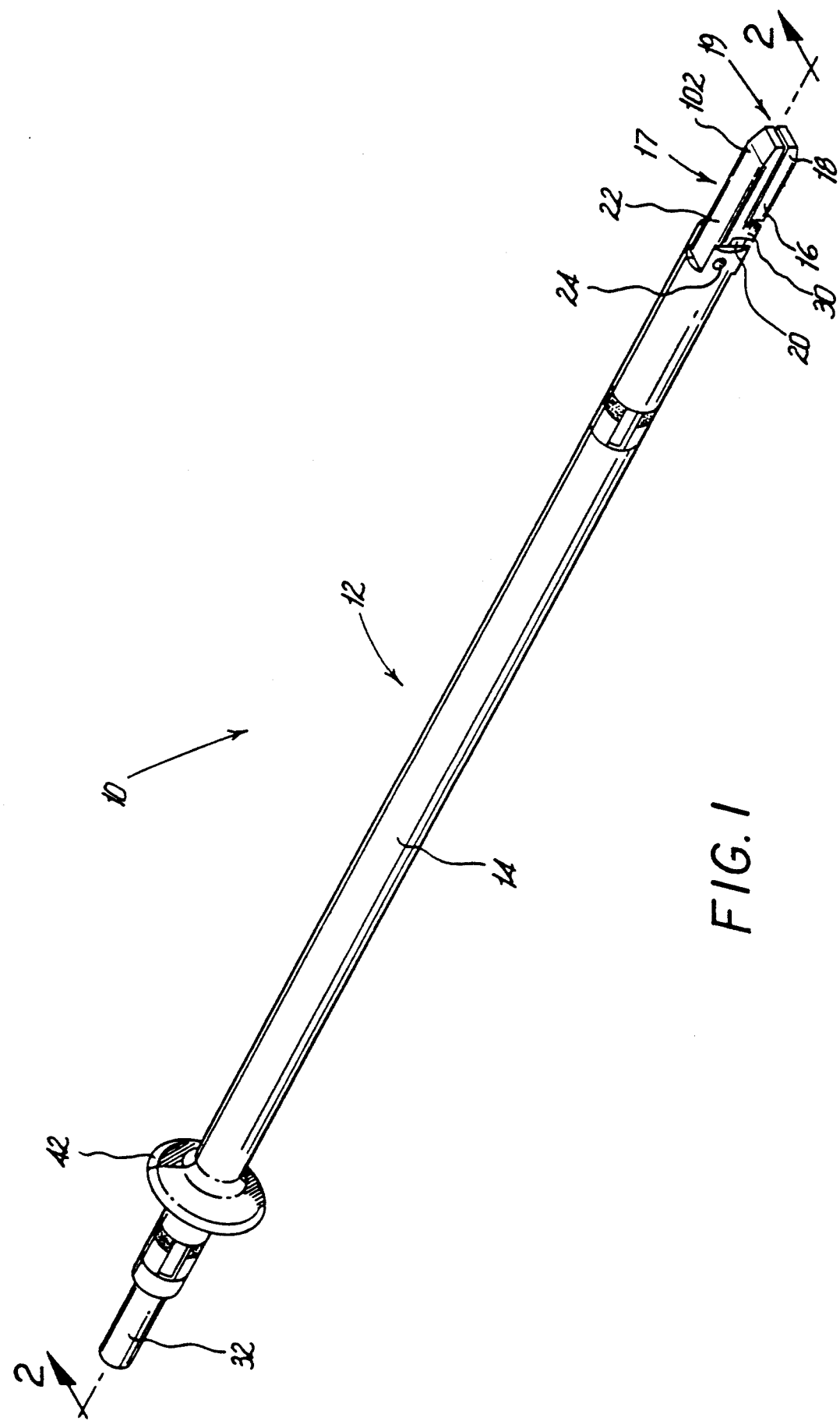
FIG. 1 is a perspective view illustrating a tissue measuring apparatus according to a first embodiment of the present invention.

Referring to FIGS. 1-9 wherein like reference numerals identify identical or similar elements, and referring initially to FIGS. 1-3 there is shown a first embodiment of a tissue measuring apparatus 10 in accordance with the present invention. The tissue measuring apparatus 10 includes a tubular body 12 having an elongated endoscopic section 14. A stationary jaw structure 16 is integrally formed at a distal end 17 of the elongated endoscopic section 14 and in axial alignment therewith. The endoscopic section 14 is configuration and dimensioned to house part of an approximation means. The stationary jaw structure 16 is generally elongated in configuration and includes a distal working end 18 and a proximal end 20.

A movable jaw structure 22 is pivotably connected at pivot point 24 to the endoscopic section 14 for pivotal approximation with the stationary jaw structure 16. The movable jaw structure 22 is generally elongated in configuration having a distal working end 26 and a proximal end 28. The movable jaw structure 22 extends distally from pivot point 24 such that when the instrument is closed the distal working ends of both the stationary and movable jaw structures 16, 22 are in mating and cooperating relation for engaging body tissue.

The distalmost ends 19 of the jaw structures 22, 16 have a rectangular cross-section, however, other configurations may be desirable, such as, for example, a square cross-section. The flat or blunted surface of the distal ends 19 of the jaw structures 22, 16 are preferred over more sharply angled or pointed surfaces. Sharply angled or pointed surfaces are less desirable because they may damage or puncture tissue during insertion or manipulation.

A scaled measurement segment 30 is an integral part of the movable jaw structure 22 and is in overlapping relation with the stationary jaw structure 16. The scaled measurement segment 30 is configured and designed to indicate measured approximation of the movable jaw structure 22 relative to jaw structure 16. Alternatively, the scaled measurement segment 30 could be integral with stationary jaw structure 16 and configured to provide an indication of the measured approximation of the movable jaw structure 22.

A remote actuation member 32 is coaxially disposed in the proximal end of the elongated endoscopic section 14. The remote actuation member 32 is configured and dimensioned as a plunger for activation of the jaw structure.

A pusher bar 34 is positioned within the endoscopic section 14 in cooperation with actuation member 32 for activating the movable jaw structure 22. The pusher bar 34 is connected at its distal end to the movable jaw structure 22 by a link 35. The link 35 is pivotably connected at pivot point 36 to the movable jaw structure 22. Pivot point 36 is below the point of rotation of the movable jaw structure about pivot point 24. The pusher bar 34 is connected at its proximal end to the remote actuation member 32 such that the pusher bar 34 is moved by distally collapsing the actuation member 32.

The endoscopic section 14 further includes a biasing spring 38 positioned between the actuation member 32 and a stop ridge 40. This stop ridge 40 provides a positive stopping position for the biasing spring 38. The spring 38 encircles the pusher bar 34 and is configured and dimensioned to allow the pusher bar 34 to move coaxially within the endoscopic section 14. The spring 38 normally biases the actuation member 32 in the proximal direction such that after depressing the actuation member 32 it will return to its original position with the jaw structure in the closed position.

A flange 42 is positioned distal to the actuation member 32 and provides a location for the fingers to grasp so that the thumb will be free to activate the actuation member 32.

Indicator sections 44, 46 are positioned distally and proximally, respectively, to the finger grip 42. The distal indicator section 44 is positioned such that it can preferably be seen in a video monitor while performing endoscopic procedures. The proximal indicator section 46 is positioned proximal to the finger grip 42 and is directly viewable when the apparatus 10 is being used in endoscopic procedures.

Both indicator sections 44, 46 function in a similar manner and include a window 48 having scale marking portions, 50, 52 respectively, located on the outer side 54 of the tubular body 12. A cursor 56 is positioned on the pusher bar 34 at predetermined locations such that, in operation, the cursor is readable against the scale marking portions to give a reading on the approximation of the jaw structure. The scale marking portions may be configured to indicate ranges such as, for example, ranges wherein particular staple or fastener sizes can be used. Alternatively, the marking portions can be more accurately graded to give direct measurements of approximation. Further, the cursor and marking portions may be reversed such that the cursor is integral with the window and the scale marking portions are positioned on the pusher bar.

Typically, the tissue measuring apparatus 10 is inserted into a cannula to access the operative site. After the jaw structures 16, 22 are moved proximate the desired body tissue, the jaw structures 16, 22 are operated to capture the body tissue therebetween.

As shown in FIGS. 2 and 3, in operation, the tissue measuring apparatus 10 in accordance with this embodiment is shown having the actuation member 32 distally depressed such that the cursor 56 shown in the window 48 has moved to correspond to scale marking portion 52 in the indicator sections 44, 46. The actuation member 32 is biased in the distal direction by compressing the biasing spring 38 against the stop ridge 40. The pusher bar 34 moves distally in concert with the actuation member 32 as indicated by the cursor 56 in the indicator sections 46, 44. The pusher bar 34 moves the link 35 in the distal direction which pivots the movable jaw structure 22 about pivot point 24 in a generally counterclockwise direction. A measured space 58 between the movable jaw structure 22 and the stationary jaw structure 16 is thus provided for positioning body tissue therebetween for measurement. Upon capture of the tissue, actuation member 32 is released causing the jaw structure to close on the tissue to be measured. The scaled measurement segment 30 provides incremented measurement of body tissue between the movable and stationary jaw structure 22, 16.

It is contemplated that a surgeon will be able to view the scaled measurement segment 30, and the distal indicator section 44 indirectly using a video monitor. The surgeon also will be able to view the proximal indicator section 46 directly while manipulating the apparatus 10 to the desired location and positioning body tissue for measurement into the space 58 between the jaw structures 22, 16.

It is also envisioned that the tissue measuring apparatus 10 can be used to measure a gap between body tissue. For example, a portion of the jaw structures 16, 22 can be inserted into the gap, and the movable jaw structure 22 approximated such that the outer surfaces 102 of the movable and stationary jaw structures 16, 22 contact the surfaces of the tissue defining the gap. A visual reading of the cursor 56 informs the surgeon as to the dimensions corresponding to the amount of approximation of the jaw structure in a similar manner as described above.

A second embodiment of the tissue measuring apparatus 11 according to the present invention is shown in FIGS. 4 and 5 and is similar to the embodiment shown in FIGS. 1-3. The second embodiment of the apparatus 11 includes a coupling member 60. The coupling member 60 is pivotably attached substantially at its center by pivot point 62 to the endoscopic section 14. The coupling member 60 is further pivotably attached to the pusher bar 34 at pivot point 64, and pivotably attached to an actuation member extension rod 66 at pivot point 68.

The actuation extension rod 66 is connected to the actuation member 32 such that when the actuation member 32 is moved distally the actuation member extension rod 66 also moves distally. The distal movement of the actuation member extension rod 66 pivots the coupling member 60 counterclockwise such that the pusher bar 34 is moved in a proximal direction.

Tissue measuring apparatus 11 further includes an indicator rod 70 pivotably connected at its proximal end at pivot point 68 to the actuation member extension rod 66, and connected at its distal end to the distal indicator section 44 by connection point 72. The indicator rod 70 thereby moves distally when the actuator member 32 is moved distally to provide a consistent display reading of tissue thickness by both indicator sections 44 and 46.

The biasing spring 38 is positioned distally to a stop wall 74 such that the biasing spring 38 is compressed when the actuator member 32 is moved distally. The biasing spring 38 normally biases the approximating member 32 in its proximal most position such that the pusher bar 34 positions the movable jaw structure 22 in a closed position in relation to the stationary jaw structure 16.

The pusher bar 34 is coaxially positioned through the endoscopic section 14 to activate the movable jaw structure 22. The distal end of the pusher bar 34 is pivotably connected to the movable jaw structure 22 as in the previous embodiment, however, the pusher bar is pivotably connected above the point of rotation of the movable jaw structure at pivot point 76. Thus, as the pusher bar 34 is moved proximally, the movable jaw structure 22 is opened in relation to the stationary jaw structure 16 creating space 58 between the jaw structures.

In operation, the tissue measuring apparatus 11 operates similarly to the previous embodiment. The actuation member 32 is moved distally which pushes the actuation member extension rod 66 distally. The indicator rod 70 moves distally via pivot point 68 which moves the mark 56 of the distal indicator section 44 in concert. Simultaneously, the coupling member 60 pivots about pivot point 62 moving the pusher bar 34 proximally via pivot point 64. The pusher bar 34 pivotably rotates the movable jaw structure 22 about pivot point 24 providing a measured space 58 between the movable jaw structure 22 and the stationary jaw structure 16 for positioning body tissue therebetween for measurement.

Referring to FIGS. 6 and 7, a third embodiment of the tissue measuring apparatus 13 is shown. Tissue measuring apparatus 13 includes the pusher bar 34 connected to a pusher block 78. The pusher block 78 includes a camming surface 80 at its distal end and communicates with the biasing spring 38 at its proximal end. The biasing spring 38 fits between the proximal end of the pusher block 78 and the distal end of the actuation member 32. The biasing spring 38 biases the actuation member 32 in an initial position having the movable jaw structure 22 in a closed relationship with the stationary jaw structure 16.

The movable jaw structure 22 includes a tab 82 at its proximal end which communicates with a jaw spring 84. The tab 82 and jaw spring 84 are configured and dimensioned such that when the camming surface 80 communicating with the tab 82 is moved distally, the tab 82 is driven downwardly against the biasing of the jaw spring 84. When the camming surface is moved proximally, the jaw spring 84, which biases the movable jaw structure 22 closed, moves the tab 82 upwardly thus pivoting the movable jaw structure 22 toward the stationary jaw structure 16.

In operation, when the actuation member 32 of the tissue measuring apparatus 13 is moved distally, the pusher bar 34 moves the pusher block 78 distally such that the camming surface 80 of the pusher block 78 moves the tab 82 in a downward direction against the biasing nature of the jaw spring 84. As the tab 82 is moved downwardly by the camming surface 80 of the pusher block 78, the movable jaw structure 22 is moved in a generally counterclockwise direction pivoting about pivot point 24. The generally counterclockwise rotation of the movable jaw structure 22 opens a space 58 between the movable jaw structure 22 and the stationary jaw structure 16. The proximal indicator section 46 and the distal indicator section 44 as well as the scaled measurement segment 30 operate essentially the same as with the first embodiment 10.

Figure 8:
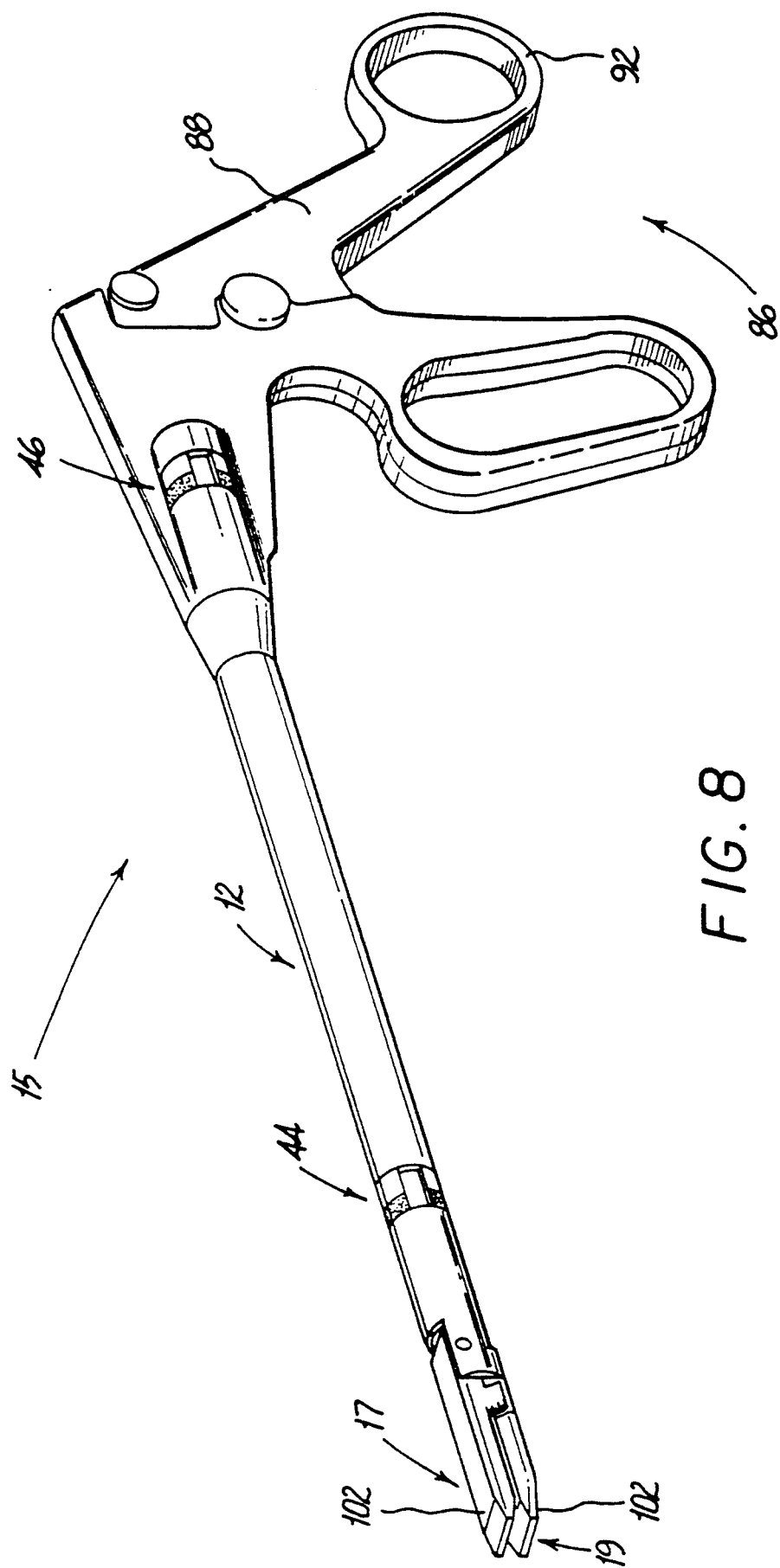
FIG. 8 is a perspective view illustrating a tissue measuring apparatus according to a fourth embodiment of the present invention having a pistol grip type handle section.
Figure 9:
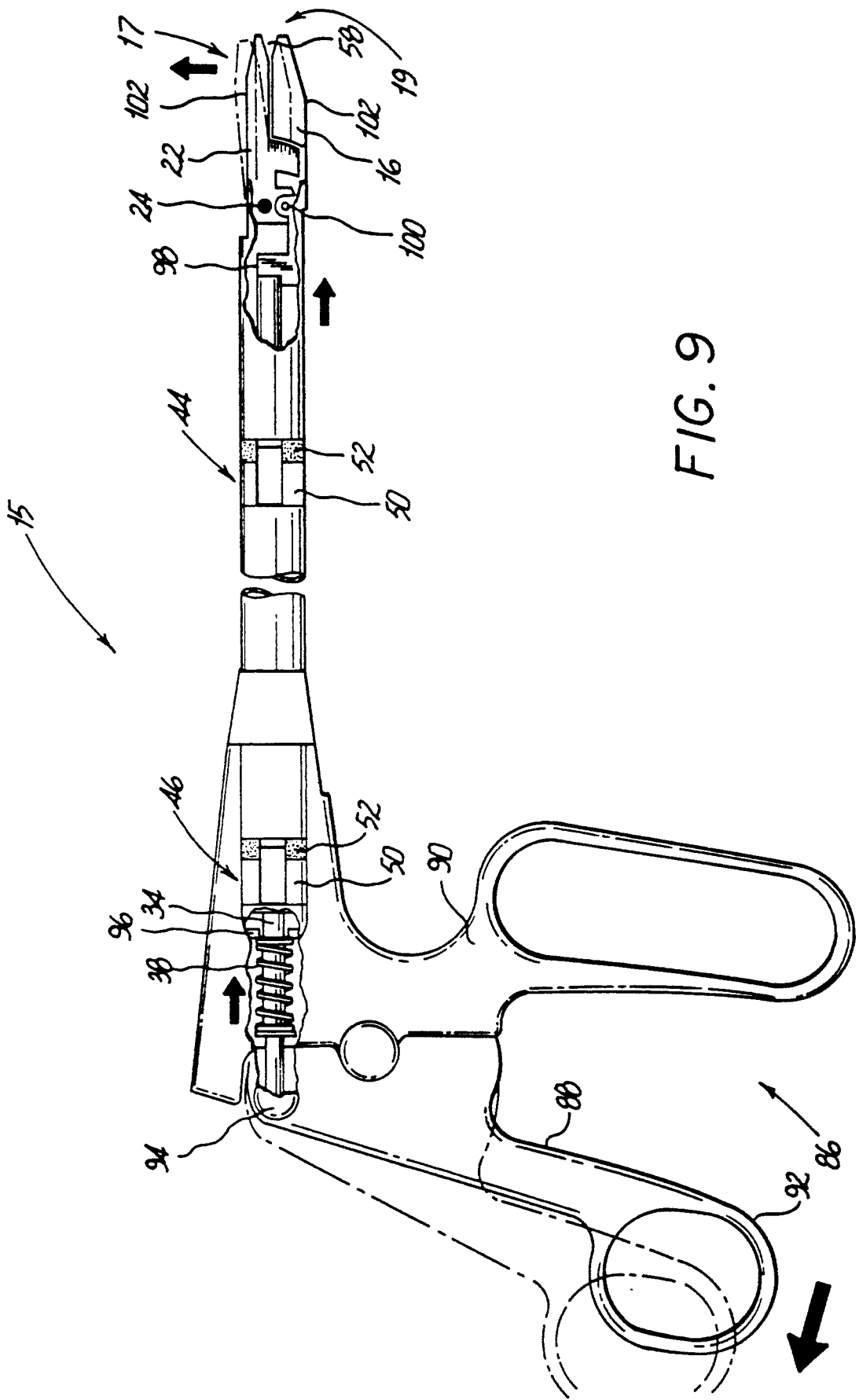
FIG. 9 is a side view in partial cut-away illustrating the tissue measuring apparatus shown in FIG. 8 showing movement of the handle section and the jaw structures in phantom.

Referring to FIGS. 8 and 9, a fourth embodiment of the tissue measuring apparatus 15 according to the present invention is shown which is similar to the embodiment shown in FIGS. 1-3. The embodiment shown in FIGS. 8 and 9 however, includes a pistol grip type handle section 86 as an embodiment of a trigger mechanism. The handle section 86 includes a pivotable portion 88 and a stationary portion 90. The pivotable portion 88 includes a ring 92 for the user's thumb such that when the pivotable portion 88 is actuated, a receiving member 94 of the pivotable portion 88 actuates the pusher bar 34 in the distal direction similarly to previous embodiments.

The biasing spring 38 is positioned between a stop wall 96 and a section of the pivotable portion 88 such that the biasing spring 38 biases the pivotable portion 88 in an initial position having the movable jaw structure 22 in a closed position in relation to the stationary jaw structure 16. The distal end of the pusher bar 34 is connected to an actuation element 98. The actuation element 98 is pivotably connected to the movable jaw structure 22 at pivot point 100 located beneath the pivotable axis 24 of the movable jaw structure 22.

In operation, the tissue measuring apparatus 15 operates in a similar manner as tissue measuring apparatus 10 described above. When the pivotable portion 88 of the handle section 86 is actuated in a generally clockwise direction, the receiving member 94 moves the pusher bar 34 in a distal direction. The pusher bar 34 distally moves the actuation element 98 distally which pivots the movable jaw structure 22 in a generally counterclockwise direction opening the space 58 between the movable jaw structure 22 and the stationary jaw structure 16.

As in the previous embodiments, the embodiment of the tissue measuring apparatus 15 described and shown in FIGS. 8 and 9 includes proximal and distal indicator section 46, 44 having corresponding scale marking portions 50, 52 which indicate the amount of the space 58 between the movable jaw structure 22 and the stationary jaw structure 16.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

I claim:

1. Apparatus for approximating jaw structure of surgical instrumentation for measuring body tissue comprising:
   an endoscopic section having a distal and a proximal end;
   first jaw structure couplable to said distal end of said endoscopic section;
   second jaw structure disposed in spaced relation to and pivotally connected with said first jaw structure, said first and second jaw structure being interconnected for substantially capturing tissue therebetween;
   means for approximating said first and second jaw structure, said means for approximating including an actuation member positioned adjacent a proximal end of said endoscopic section; and
   measuring means for indicating movement of said first and second jaw structures wherein said actuation member remotely actuates said jaw structures to permit working interaction between said first and said second jaw structures, the interaction resulting in registration of at least one measurement on said measuring means.

2. Apparatus according to claim 1 wherein said means for approximating includes a pusher means slidably positioned within said endoscopic section and being couplable to said actuation member and at least one of said first and second jaw structures.

3. Apparatus according to claim 2, wherein said pusher means is pivotally coupled to said second jaw structure.

4. Apparatus according to claim 1 further comprising means for remotely indicating the relative approximation of said jaw structure.

5. Apparatus according to claim 1, wherein said first jaw structure is couplable to said second jaw structure by means of a pivot pin.

6. Apparatus according to claim 1, wherein longitudinal distal movement of said actuation member causes a counter-clockwise rotation of said second jaw structure.

7. Apparatus according to claim 1, wherein said first and said second jaw structures have first and second tissue engaging surfaces, respectively, said first and said second tissue engaging surfaces being blunt.

8. Apparatus for approximating jaw structure of surgical instrumentation for measuring body tissue comprising:
   an elongated endoscopic section having a distal and a proximal end;
   stationary jaw structure couplable to said distal end of said endoscopic section, said stationary jaw structure having a distal working end and a proximal end;
   movable jaw structure having a distal working end and a proximal end, said movable jaw structure being pivotally couplable to said stationary jaw structure and disposed in spaced relation to said stationary jaw structure for measured interaction with said distal working end of said stationary jaw, said movable jaw structure and said stationary jaw structure being designed and adapted for capturing body tissue between said distal working ends of said stationary and said movable jaw structure;
   means for approximating said movable jaw structure in relation to said stationary jaw structure permitting measured working interaction between said distal working ends of said movable and stationary jaw structure; and
   means for indicating relative approximation of said movable jaw structure.

9. Apparatus according to claim 8 wherein said movable jaw structure is pivotably mounted to said stationary jaw structure.

10. Apparatus according to claim 8 wherein said movable jaw structure is pivotable about an axis orthogonal to said proximal end of said stationary jaw structure.

11. Apparatus according to claim 8 wherein said movable jaw structure is manually and selectively positionable with respect to said stationary jaw structure.

12. Apparatus according to claim 8 further comprising means for remotely indicating the relative approximation of said jaw structure.

13. Apparatus according to claim 8 wherein said indicating means includes the use of color coding to indicate the relative approximation of said jaw structure.

14. Apparatus according to claim 8 wherein said indicating means includes a measuring element providing indication of movement of said movable jaw structure.

15. Apparatus according to claim 8 wherein said indicating means includes a first indicator positionable about the endoscopic section and a second indicator positioned adjacent a proximal end of said elongated endoscopic section of said instrument.

16. Apparatus according to claim 8 wherein said means for approximating includes pusher means slidably positioned within said endoscopic section and said pusher means being coupled to said remote actuation member and said movable jaw structure.

17. Apparatus according to claim 16 wherein said approximation means includes an actuation member positioned remotely from said jaw structure for selectively and manually moving said pusher means.

18. Apparatus according to claim 8 further comprising means for biasing said pusher means such that said stationary jaw structure and said movable jaw structure is normally biased in a closed position.

19. Apparatus according to claim 8 wherein said approximation means includes an actuation member coupled to said proximal end of said elongated endoscopic section for manually and selectively approximating said movable jaw structure.

20. Apparatus according to claim 8 wherein said approximation means includes a handle section, said handle section includes an actuating member coupled to said proximal end of said endoscopic section for manually and selectively approximating said movable jaw structure.

21. Apparatus according to claim 20 wherein said approximation means further includes a pusher bar connected at one end to said actuating member of said handle section and at another end to said movable jaw structure such that said handle section manually and selectively approximates said movable jaw structure.

22. Apparatus according to claim 21, wherein said pusher bar is connected at a distal end to a linking member, said linking member being pivotably attached to said movable jaw structure below an axis of rotation of said movable jaw structure such that distal movement of said actuation member provides pivotal movement of said movable jaw structure.

23. Apparatus according to claim 21, wherein said distal end of said pusher bar is pivotably connected to said movable jaw structure above a plane horizontally passing through an axis of rotation of said movable jaw structure, and said approximation means includes a coupling member pivotably connected at substantially its center to said elongated endoscopic section, said coupling member being connected at one end to said actuating member and at another end to said pusher bar such that moving said actuation member towards said distal end of said elongated endoscopic section pivotably rotates said movable jaw structure.

24. Apparatus according to claim 22, further comprising a rod element attached at one end to said actuation member and at another end to a distally positioned means for visually indicating motion of said movable jaw structure.

25. Apparatus according to claim 21, wherein said approximation means further includes a tapered member contacting at a proximal end said pusher bar, said tapered member having a distal inclined surface contacting said movable jaw structure such that moving said approximation means distally with respect to said elongated endoscopic section pivotably rotates said movable jaw structure about a rotational axis to an open position, and said movable jaw structure rotates against an opposing force of a means for biasing said movable jaw structure in a closed position.

26. Apparatus according to claim 8, further comprising an outwardly extending circumferential flange adjacent said proximal end of said elongated endoscopic section.

* * * * *